(12) United States Patent
Seeh

(10) Patent No.: US 7,981,130 B2
(45) Date of Patent: Jul. 19, 2011

(54) MEDICAL INSTRUMENT FOR CUTTING BIOLOGICAL AND ESPECIALLY HUMAN TISSUE

(75) Inventor: Daniel Seeh, Immendingen (DE)

(73) Assignee: Karl Storz GmbH & Co. KG (DE)

( * ) Notice: Subject to any disclaimer, the term of this patent is extended or adjusted under 35 U.S.C. 154(b) by 968 days.

(21) Appl. No.: 11/314,278

(22) Filed: Dec. 21, 2005

(65) Prior Publication Data
US 2006/0189920 A1 Aug. 24, 2006

Related U.S. Application Data

(63) Continuation of application No. PCT/EP2004/009997, filed on Sep. 8, 2004.

(30) Foreign Application Priority Data

Dec. 11, 2003 (DE) .................................. 103 58 279

(51) Int. Cl.
*A61B 17/32* (2006.01)
(52) U.S. Cl. ........................................ 606/180; 606/167
(58) Field of Classification Search .................. 600/131, 600/114, 156; 604/22; 606/167, 80, 205, 606/159, 84, 170, 179, 180, 184
See application file for complete search history.

(56) References Cited

U.S. PATENT DOCUMENTS

| 5,123,904 | A | | 6/1992 | Shimomura et al. | ............ 604/22 |
|---|---|---|---|---|---|
| 5,618,296 | A | * | 4/1997 | Sorensen et al. | .............. 606/180 |
| 5,658,304 | A | * | 8/1997 | Lim | ............................... 606/176 |
| 6,039,748 | A | * | 3/2000 | Savage et al. | .................. 606/180 |
| 6,173,802 | B1 | * | 1/2001 | Kodaira et al. | ............... 180/444 |
| 6,193,715 | B1 | * | 2/2001 | Wrublewski et al. | ........... 606/45 |
| 6,347,477 | B1 | * | 2/2002 | Hopper | ............................. 43/20 |
| 6,439,541 | B1 | | 8/2002 | Nösel et al. | ................. 251/149.1 |
| 6,572,632 | B2 | * | 6/2003 | Zisterer et al. | ................. 606/170 |
| 6,629,570 | B1 | * | 10/2003 | Head | ............................... 175/61 |
| 6,638,238 | B1 | | 10/2003 | Weber et al. | .................... 604/22 |
| 6,780,189 | B2 | * | 8/2004 | Tidwell et al. | .................. 606/80 |
| 6,837,644 | B2 | * | 1/2005 | White et al. | .................. 403/337 |

(Continued)

FOREIGN PATENT DOCUMENTS

DE 43 06 205 C1 10/1994

(Continued)

OTHER PUBLICATIONS

International Search Report, Feb. 11, 2005, (5 pages).

*Primary Examiner* — Anhtuan T Nguyen
*Assistant Examiner* — David Eastwood
(74) *Attorney, Agent, or Firm* — St. Onge Steward Johnston & Reens LLC

(57) ABSTRACT

The invention relates to a medical instrument for cutting biological and especially human tissue, having a hollow cutting tube that can rotate by means of an engine around its longitudinal axis, on whose distal end at least one blade is mounted, as well as with a handle in which the cutting tube is mounted for control purposes. In order to produce a medical instrument for cutting biological and especially human tissue in which the powering of the cutting tube is of simple construction and involves minor losses of capacity, it is proposed with the invention that the engine is configured as a hollow-shaft engine mounted on the cutting tube.

19 Claims, 8 Drawing Sheets

U.S. PATENT DOCUMENTS

| | | | |
|---|---|---|---|
| 7,232,439 B2 * | 6/2007 | Ciarrocca | 606/48 |
| 2007/0219549 A1 * | 9/2007 | Marshall et al. | 606/34 |
| 2008/0039883 A1 * | 2/2008 | Nohilly | 606/180 |
| 2008/0058846 A1 * | 3/2008 | Vosough | 606/180 |
| 2008/0065129 A1 * | 3/2008 | Batchelor et al. | 606/172 |
| 2008/0255597 A1 * | 10/2008 | Pravong et al. | 606/169 |

FOREIGN PATENT DOCUMENTS

| | | |
|---|---|---|
| DE | 199 16 144 A1 | 3/2000 |
| EP | 0 555 803 B1 | 8/1993 |
| EP | 0 769 278 A2 | 4/1997 |
| EP | 0 806 183 A1 | 11/1997 |
| WO | WO 02/83006 A2 | 4/2002 |

* cited by examiner

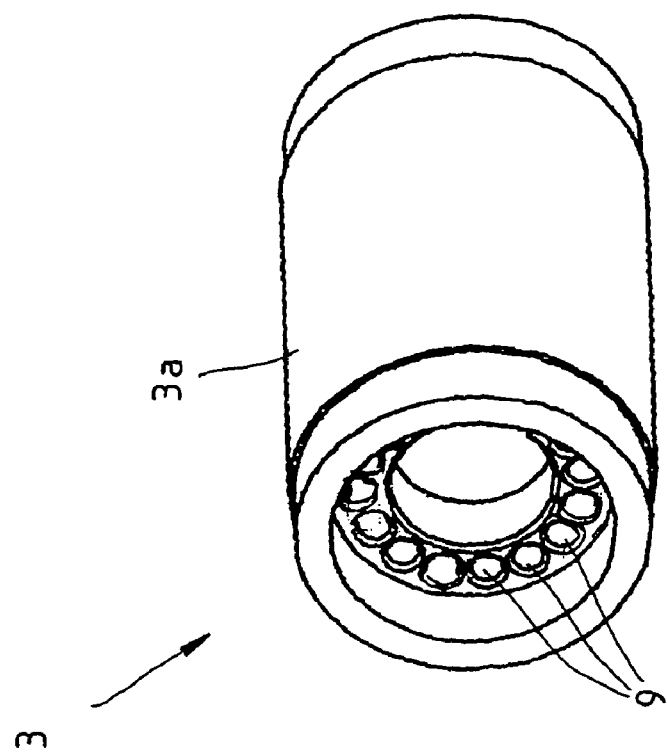
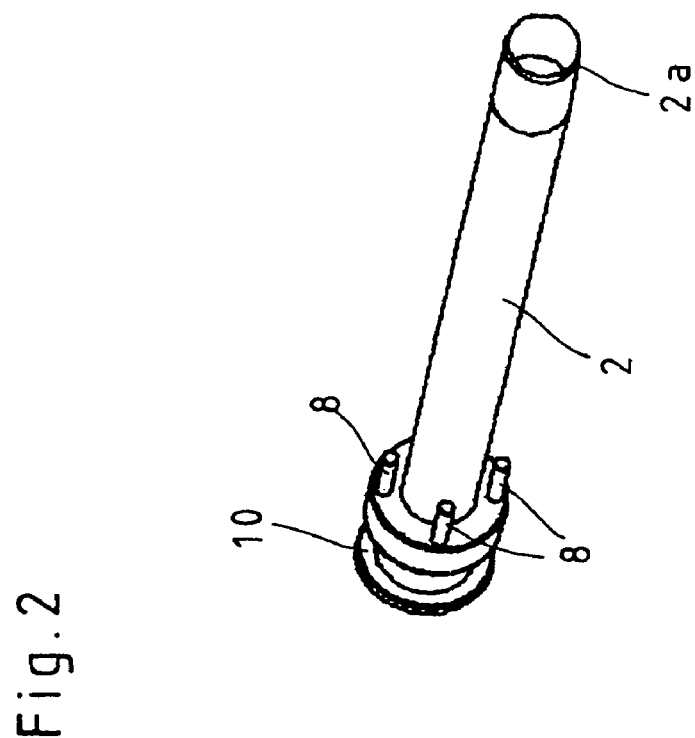
Fig. 2

MEDICAL INSTRUMENT FOR CUTTING BIOLOGICAL AND ESPECIALLY HUMAN TISSUE

CROSS-REFERENCE TO RELATED APPLICATIONS

The present application is a continuation of pending International patent application PCT/EP2004/009997 filed on Sep. 8, 2004 which designates the United States and claims priority of German patent application 103 58 279.7 filed on Dec. 11, 2003.

FIELD OF THE INVENTION

The invention relates to a medical instrument for cutting biological and especially human tissue, having a hollow cutting tube that can rotate around its longitudinal axis by means of an engine and with at least one blade situated on the tube's distal end, as well as having a handle in which the cutting tube is positioned so that it can be guided. In addition the invention relates to an insulation providing gas-proof insulation of the instrument.

BACKGROUND OF THE INVENTION

Instruments of this type, called morcellators, are used in endoscopic interventions required for the removal of large portions of tissue. These morcellators consists of a powered cutting tube, which can be introduced directly into the body or into a natural or artificially produced body cavity. To remove tissue, a gripping pincer is introduced through the cutting tube into the body or body cavity to grasp the tissue that is to be removed. If the pincer is then withdrawn and if the tissue is pressed against the cutting edge of the rotating morcellator, a cylindrically shaped block of tissue can be cut out and removed through the tube by carefully measured pulling and possibly varying the rotation speed and rotation direction. Even large amounts of tissue can be extracted in this way within a few minutes.

Generic medical instruments are described for instance in EP-B1-0 555 803 and EP-A1-0 806 183. In these morcellators known from the art, the rotating drive of the cutting tube is carried out by a tooth-wheel and/or worm gear held in place between the motor and the cutting tube.

The use of these gears which serve to transmit the rotation force, however, can cause considerable capacity losses in the actual motor power. In addition the drives are sometimes very complex in structure and thus also quite expensive.

SUMMARY OF THE INVENTION

Consequently, it is the object of the invention to improve a medical instrument of the aforementioned type in such a way that the powering of the cutting tube is of simple and space-saving construction and incurs low capacity losses.

This object is fulfilled by the invention in that the engine is configured as a hollow-shaft engine positioned on the cutting tube.

Through the inventive use of a hollow-shaft engine positioned on the cutting tube, as known in the art for air-conditioning fan drives, it is possible to configure the drive so that it is extremely compact and space-saving.

According to a preferred embodiment of the invention, the hollow-shaft engine powers the cutting tube directly without gears, so that the capacity losses of the drive motor can be clearly reduced. In addition the gearless configuration of the drive considerably simplifies the manufacture and installation.

According to a first practical embodiment of the invention it is proposed that the cutting tube and the hollow-shaft engine are coupled together by means of rods, which run in the axial direction of the cutting tube, are mounted on the cutting tube and/or on the hollow-shaft engine, and can be inserted into corresponding openings in the other respective component. These rods, together with the corresponding openings, allow a form-locking and spring-locking coupling of the drive and the cutting tube.

To permit uniform powering of the cutting tube, it is proposed that four rods should be positioned on the cutting tube distributed evenly around the longitudinal axis of the cutting tube and running in the axial direction of the cutting tube. However openings are also possible with fewer rods, such as three or with more than four rods.

According to the invention the installation of the coupling of the two components can be simplified if more than four openings are configured on the hollow-shaft engine for insertion of the rods so that the components can be coupled with one another in various positions with respect to one another.

It is further proposed with the invention that the rods coupling the cutting tube and the hollow-shaft engine to one another are positioned on an adapter that can be secured to the cutting tube.

According to a second practical embodiment of the invention it is proposed that the hollow-shaft engine is configured as an outer rotor motor. The outer rotor engine is distinguished in that the engine's rotor is not positioned lying inward as is customary with other electrical machines but rather outward, that is, surrounding the stator.

The inventive use of the outer rotor engine is especially advantageous because it is possible to configure the engine in such a way that the rotor of the outer rotor engine coaxially surrounds the cutting tube and the cutting tube forms the stator of the outer rotor engine. The configuration of the cutting tube as part of the cutting tube drive allows an especially compact structure with minimal capacity losses of the motor performance. To cause the cutting tube, which actually forms the stator of the outer rotor engine, to be powered by turning around its longitudinal axis, it is proposed with the invention that during operation the user grasping the handle forms a torque support for the outer rotor engine in such a way that from this point the rotatably mounted cutting tube forms the rotor of the outer rotor engine.

The configuration of the cutting tube drive with the cutting tube as stator of the outer rotor engine, according to a practical embodiment of the invention, can be achieved if the cutting tube consists of a magnetizable material and the winding of the outer rotor engine is positioned so that it coaxially surrounds the cutting tube.

Finally, it is proposed with the invention that the cutting tube is mounted in the handle by means of at least one bearing, especially a ball bearing, in order to ensure low-friction rotation of the cutting tube. Through the pressure of the cutting tube against the tissue that is to be morcellated, the cutting tube is also impacted with axially acting forces, and therefore it is further proposed with the invention that at least one bearing is configured as an angular contact ball bearing exposed to axial forces or as a taper roller bearing.

On the one hand, to allow the introduction of the cutting tube into the operating area and, on the other hand, to protect tissue that is not to be treated from being cut, according to a preferred embodiment of the invention, the cutting tube is positioned on the distal side in a trocar sleeve that coaxially surrounds the cutting tube.

To make it possible, during the operation, to insert at least one additional medical instrument, for instance a gripping pincer for grasping tissue to be morcellated, into the hollow cutting tube, the cutting tube includes a central passage bore hole.

The invention also relates to a medical instrument for cutting biological and especially human tissue having a central canal extending along the longitudinal axis for inserting a hollow cutting tube that can rotate around its longitudinal axis by an engine, and on the distal end of this cutting tube at least one blade is positioned, and for inserting at least one additional medical instrument that can be introduced into the hollow cutting tube, in such a way that at least one insulation agent is foreseen to insulated the central canal against gas.

Because, in endoscopic operations of the abdominal area, it is customary to fill the abdominal area with gas to extend the operating area and to form a pneumo-peritoneum, the hollow central canal can be closed off by at least one insulation agent so that the gas cannot escape from the abdominal area, for instance by way of a trocar sleeve.

According to a first embodiment of the invention, it is proposed that the at least one insulation agent takes the form of an insulating cap that can be secured on the proximal end of the central canal. This manner of configuration of the insulation agent constitutes an especially simple and easily installed embodiment, in which the insulation cap advantageously takes the form of a one-time valve consisting of an autoclavable material.

According to a practical embodiment of the invention, the insulation cap is configured as a membrane that can be perforated by a medical instrument that can be inserted into the central canal. With this insulation cap configured as a one-time valve, the perforated membrane material adheres with insulating effect against the outside of the medical instrument that is to be inserted into the central canal.

According to an alternative embodiment of the invention, it is proposed that an opening is formed in the insulation cap that can be widened by the medical instrument that is to be inserted into the central canal.

According to a second embodiment of the invention, it is proposed that the at least one insulation agent is configured as a flap valve that can be inserted into the central canal. This flap valve can of course also be used in addition to the additional insulation agents, such as the insulation cap that can be secured on the proximal side.

According to a practical embodiment of the invention, the flap valve has two flap wings directed toward the distal end of the central canal and contiguous to one another, in such a way that the flap valve insulates the central canal when the cutting tube is not inserted into the central canal or has been withdrawn from it. The angle at which the two flap wings of the flap valve are contiguous to one another is advantageously less than the angle of the blade on the distal end of the cutting tube. Through the choice of this angle of the flap wings that are contiguous to one another in a beak shape, it can be ensured, when the cutting tube is pushed through, that the blade of the cutting tube does not collide with the flap wings to open the flap wings, but instead the proximal ends of the tapering blade open the flap wings primarily in a radial direction outward.

It is further proposed with the invention that in the area of the distal end of the additional medical instrument that is to be inserted into the cutting tube, a thickened area is configured in such a way that the outer diameter of this thickened area corresponds to the inner diameter of the cutting tube, in particular in the area of the blade. This thickened area forms an insulation agent to insulate the hollow cutting tube.

Because, on introducing an inventive medical instrument into the operating area, it can occur that tissue that is not to be treated comes into contact with the blade of the cutting tube and is damaged by the sharp cutting edge, according to another embodiment of the invention the insulating agent configured as a thickened area on the additional medical instrument can be used as a cutting edge guard, which, when the cutting tube is introduced into the operating are, can be brought radially flush into contact with the cutting edge of the blade and locks in axial direction at least flush with the cutting edge of the blade.

It is finally proposed with the invention that, to configure the central canal, the instrument includes at least one trocar sleeve positioned on the distal side, an engine configured as a hollow-shaft engine and equipped with a central opening for the cutting tube that is to be powered, and a handle mounted on the proximal side and equipped with a central passage bore hole.

It is possible to facilitate control of the inventive instrument for the operator if an additional, angled hand piece can be secured on the handle. This additional hand piece is advantageously is at a 90-degree angle to the instrument's longitudinal axis and is weight-optimized.

Additional characteristics and advantages of the invention can be seen from the associated illustration, which depicts various embodiments of an inventive medical instrument for cutting biological and especially human tissue merely in schematic form.

BRIEF DESCRIPTION OF THE DRAWINGS

FIG. 2 shows an enlarged detail view of an inventive coupling between cutting tube and engine according to a second embodiment of the invention.

DETAILED DESCRIPTION OF THE INVENTION

Figure 1:
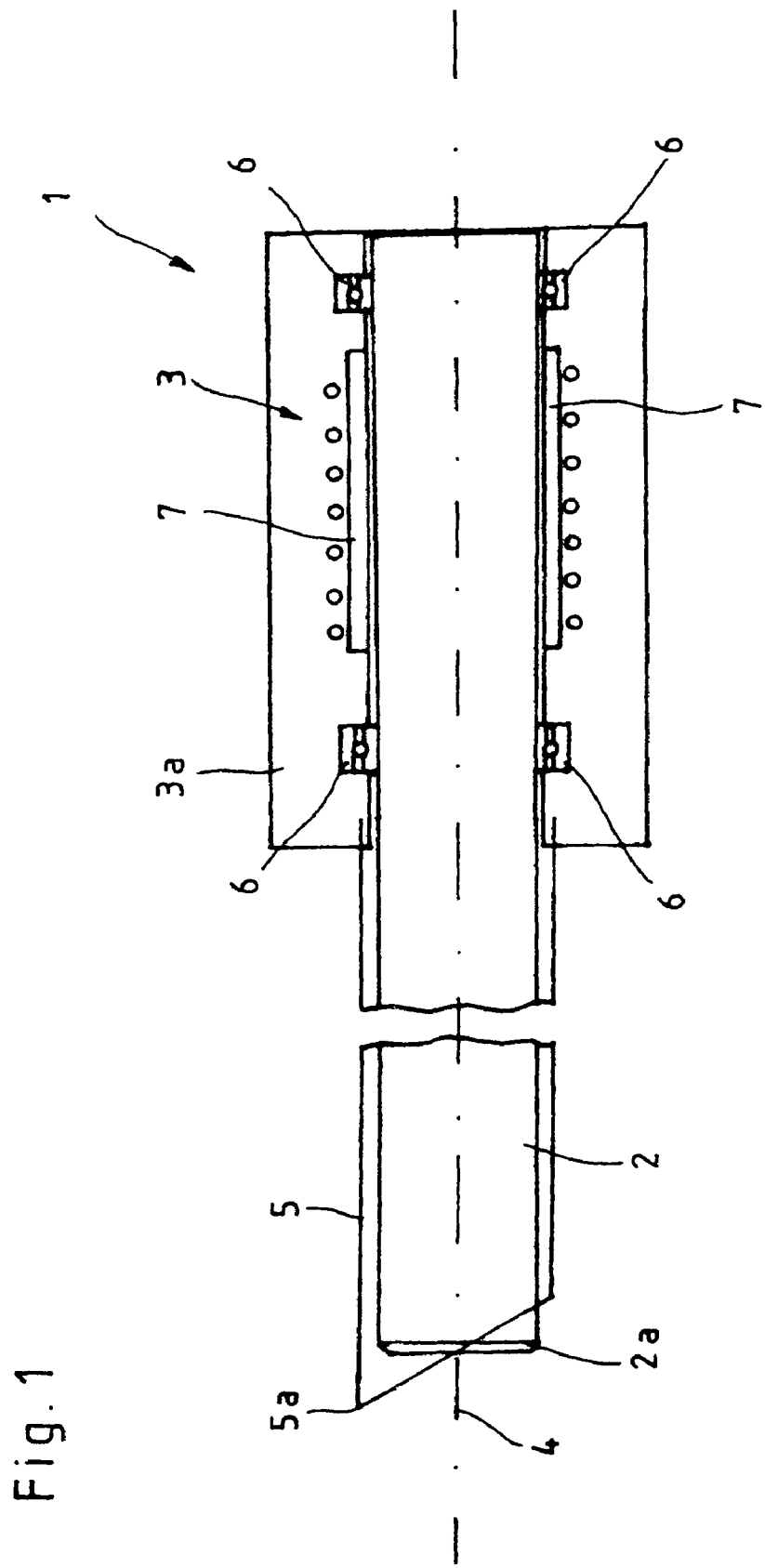
FIG. 1 shows a portion of a schematic longitudinal section through a first embodiment of an inventive medical instrument.

The medical instrument depicted in the illustrations, configured as a morcellator, for cutting biological and especially human tissue consists essentially of a hollow cutting tube mounted rotatably in a handle 1 as well as an engine 3 by which the cutting tube 2 can be powered to rotate around its longitudinal axis 4. For cutting the tissue the cutting tube 2 on the distal end has a blade 2a. The handle 1 is formed in the illustrated embodiment from an engine housing 3a of the engine 3.

As can be further seen from the illustration, the cutting tube 2 in the illustrated embodiment is coaxially surrounded, at least in its area on the distal side of the handle 2, by an outer tube formed for instance as a trocar sleeve 5, whose distal end, while forming a point 5a running at an angle in the longitudinal direction, in such a way that the trocar sleeve 5 overhangs the cutting tube 2 at least in the area of the point 5a on the distal side. Besides holding open the access way to the operating area, the trocar sleeve 5 serves to allow cover at least partially the blade 2a of the cutting tube 2, for instance upon introducing the morcellator into the operating area, in order to cause no unintentional damage on tissue that is to be protected. The trocar sleeve 5 is advantageously configured in such a way that it can be mounted between a position concealing the blade 2a and a position exposing the blade 2a in the direction of the longitudinal axis 4 of the cutting tube 2.

It is also possible of course to configure the cutting tube 2 in such a way that it can be mounted between a position overhanging the point 5a of the trocar sleeve 5 and a position withdrawn behind the point 5a of the trocar sleeve 5 in the direction of the longitudinal axis of the instrument.

In addition to the illustrated use of a angular or pointed trocar sleeve 5 equipped with a point 5a, it is of course also possible to equip a morcellator of the above-described type with a straight or blunt trocar sleeve 5, which has a straight closing on the distal side.

To mount the cutting tube 2 to rotate in the handle 1 (the engine housing 3a) with the least possible friction, in this embodiment two bearings 6 are provided as ball bearings, of which at least one is advantageously configured as an angular contact ball bearing in order to be able to assume forces that also act in axial direction.

The engine 3 for rotating driving of the cutting tube 2 is configured as an engine housing 3a configured as a hollow-shaft engine positioned on the cutting tube 2 in the area of the engine housing 3a configured as a handle 1, by which the cutting tube 2 can be powered directly, that is, gearlessly.

In the embodiment illustrated in FIG. 1, the hollow-shaft engine is configured as an outer rotor engine, in such a way that a rotor 7 equipped with the winding coaxially surrounds the cutting tube 2 that serves as stator of the engine 3 and is made of magnetizable material.

In the operation of a morcellator with this configuration, the operator of the morcellator, griping the handle 1 (the engine housing 3a) with one hand, acts as the torque support for the engine 3. Because the rotor 7 is positioned in the handle 1, this gripping of the rotor 7 of the outer rotor engine causes the cutting tube 2 now to constitute the rotating part of the engine 3 and rotate around its longitudinal axis 4.

FIG. 2 shows an alternative embodiment of the cutting tube drive. In this embodiment the engine 3 is again configured as a hollow-shaft engine positioned on the cutting tube 2, but the engine 3 and the cutting tube 2 are coupled with one another in form-locking and spring-locking manner by rods 8, running in the axial direction of the cutting tube 2 and mounted on the cutting tube 2, which rods can be inserted into corresponding openings 9 on the engine 3. As can also be seen from FIG. 2, the rods 8 are positioned on an adapter 10 mounted on the cutting tube 2.

To allow coupling that is uniform and also essentially free of imbalance, four rods 8 are positioned at equal distances around the longitudinal axis of the cutting tube 2 on the cutting tube 2 or on the adapter 10. Installation of the coupling of the two components 2 and 3 can be simplified if more than four openings 9 are configured on the engine 3 for inserting the rods 8, so that the components 2 and 3 can be coupled together in various positions with respect to one another.

Of course it is also possible to configure the coupling between the engine 3 and the cutting tube 2 in such a way that the rods 8 are situated on the engine 3 and the openings 9 for inserting the rods 8 are situated on the cutting tube 2 or on the adapter 1 0 that is secured on the cutting tube 2. Openings with fewer rods 8, particularly three rods 8, or with more than four rods 8 are also possible.

The use of the hollow-shaft engine placed directly on the cutting tube 2 represents a form of cutting tube drive that is especially economical in terms of space and easy to produce and install. In addition, thanks to the gearless direct powering of the cutting tube 2, losses of capacity in the transmission of the engine torque to the cutting tube 2 can be most extensively minimized.

Figure 3:
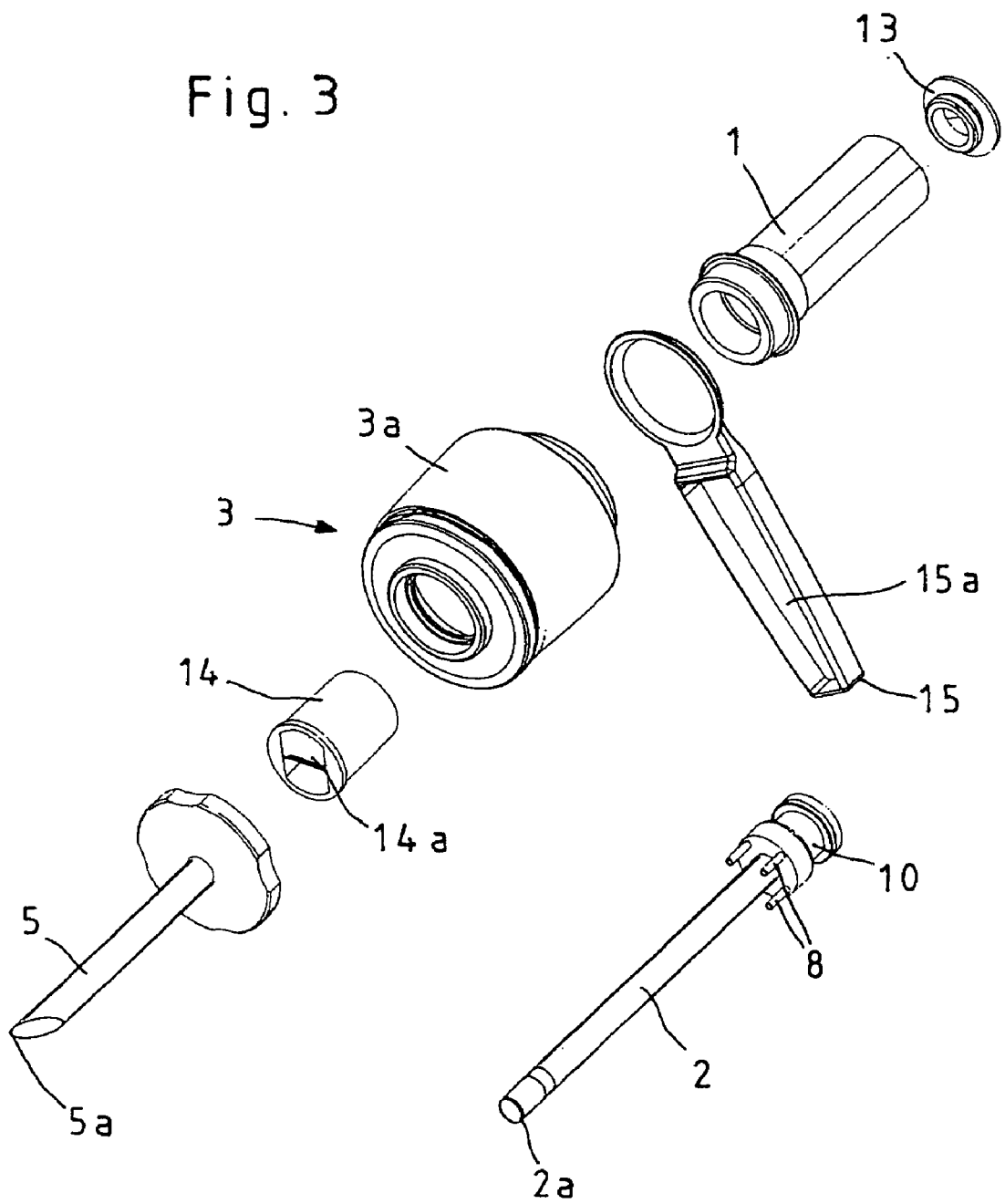
FIG. 3 shows a perspective exploded view of a first practical embodiment of an inventive instrument.
Figure 6:
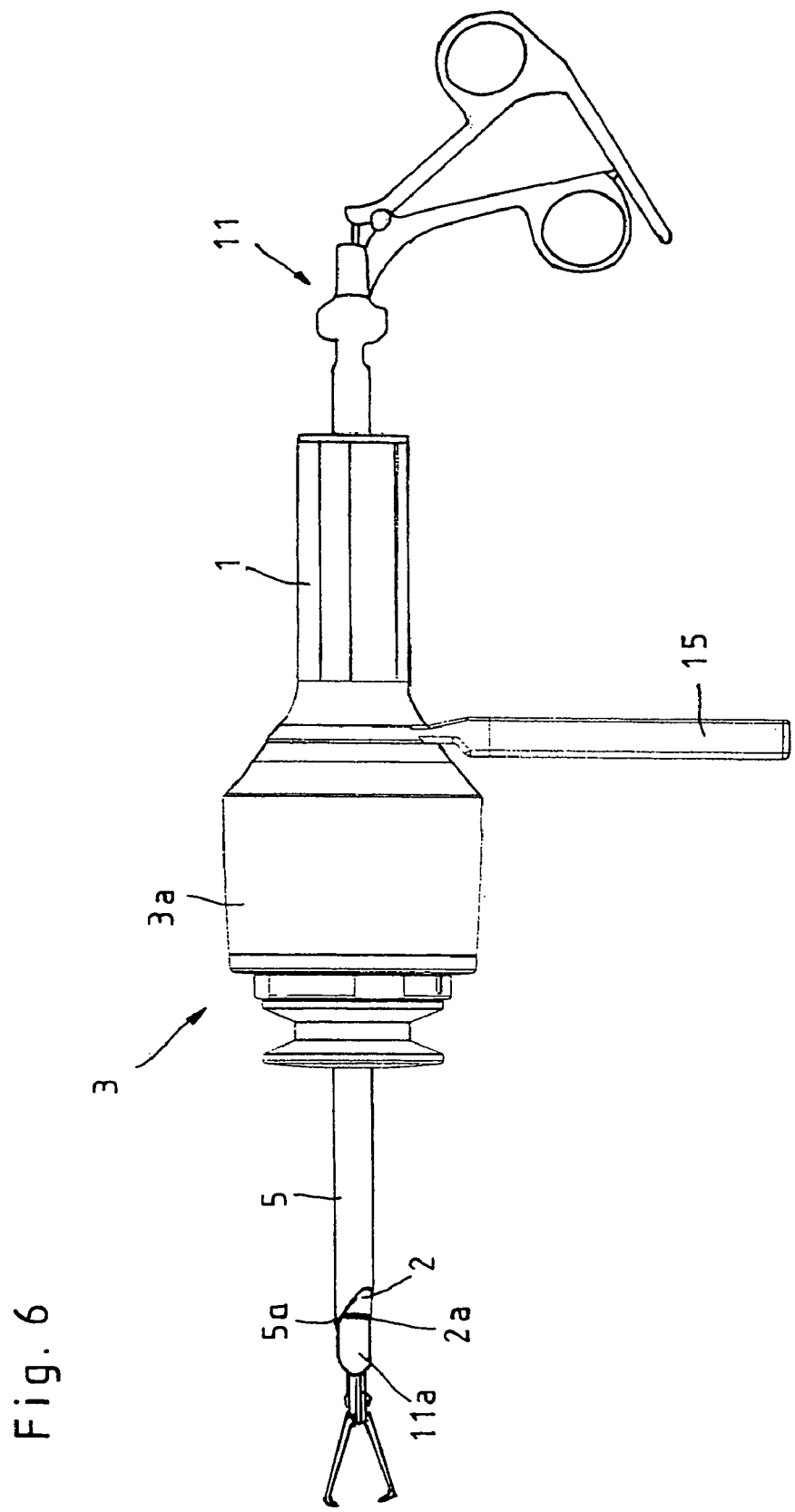
FIG. 6 shows a side view according to FIG. 4 but showing the instrument with an inserted additional instrument.

FIGS. 3 and 6 depict a first practical embodiment for forming a medical instrument for cutting biological and especially human tissue, which is configured as a morcellator for laparoscopic interventions. As can be seen in particular from the exploded view in FIG. 3, the illustrated morcellator consists essentially of an engine housing 3a of the engine 2, configured as a hollow-shaft engine, which sleeve 3a simultaneously forms the morcellator sleeve; of a handle 1 positioned on the proximal side on the engine housing 3a; of the trocar sleeve 5 on the distal side; and of the cutting tube 2 mounted inside the engine housing 3a and inside the trocar sleeve 5.

For inserting an additional medical instrument 11, as illustrated in FIG. 6, the morcellator has a central canal 12 extending along the longitudinal axis 4 of the morcellator, which can be configured thanks to the central passage bore hold la in the handle 1. This central canal 12 can be seen in particular from the sectional depiction of FIG. 5.

In endoscopic operations in the abdominal area, because it is customary to fill the abdominal area with gas to widen the operating space and to form a pneumo-peritoneum, the hollow central canal 12 can be locked by at least one insulation agent so that the gas cannot escape from the abdominal area, for instance through the trocar sleeve 5 and the central canal 12.

In the embodiment illustrated in FIGS. 3 to 6, two insulation agents are provided for gas-proof insulation of the central canal 12, namely, first, an insulation cap 13 that can be secured on the proximal end of the central canal 12 and, second, a flap valve 14 that can be inserted into the central canal 12. Both insulation agents 13 and 14 can be used independently of one another and in combination with one another.

Figure 5:
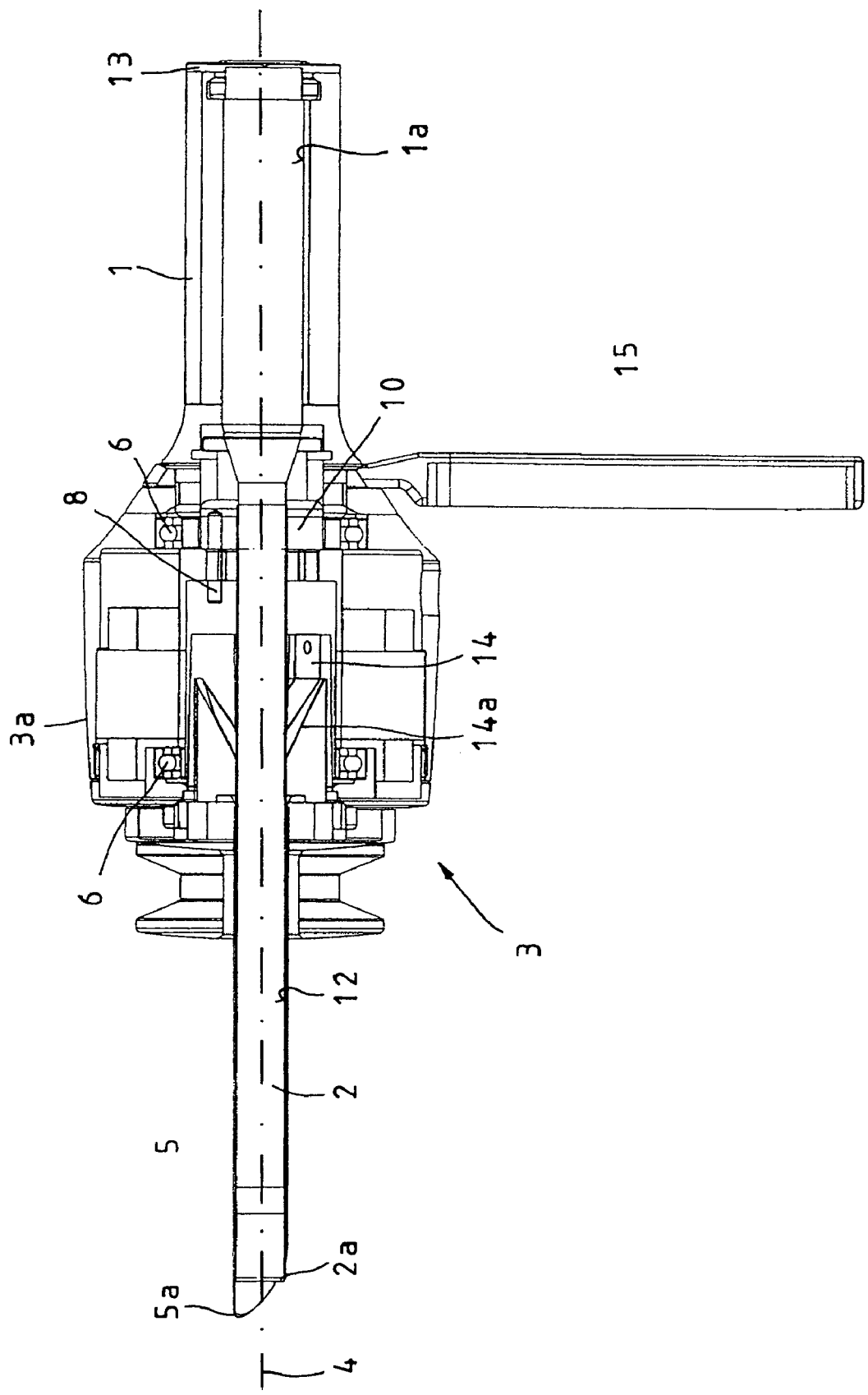
FIG. 5 shows a longitudinal section through the instrument according to FIG. 4.
Figure 8:
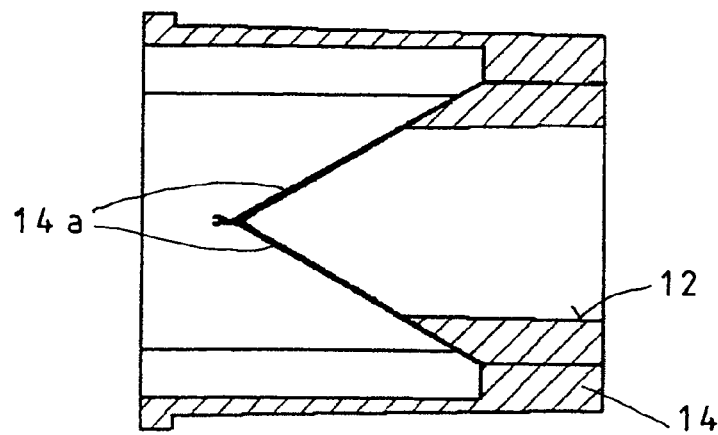
FIG. 8 shows a schematic longitudinal section through an inventive flap valve in the closed position.
Figure 9:
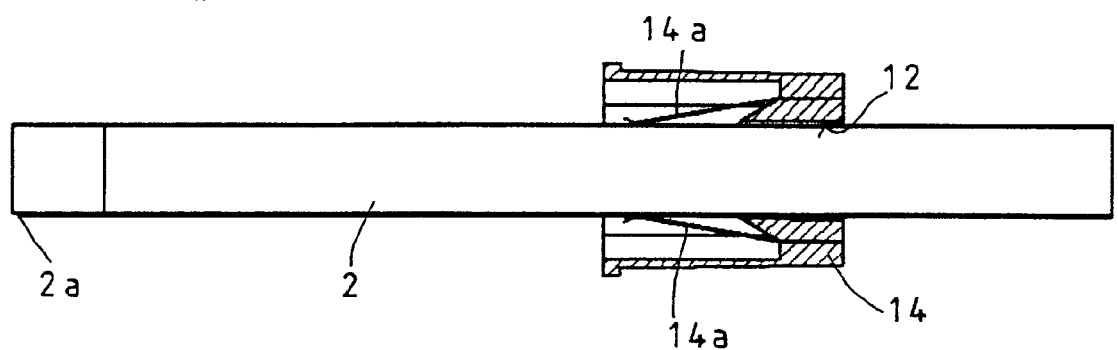
FIG. 9 shows a longitudinal section corresponding to FIG. 8 but depicting the flap vale in the close position with the cutting tube inserted.

The structure and operating manner of the flap valve 14 can be seen in particular in the schematic sectional drawings of FIGS. 8 and 9 as well as in the longitudinal section of FIG. 5. As shown in the view in FIG. 8, the flap valve 14 has two flap wings 14a that point toward the distal end of the central canal 12 and that in the closed position (FIG. 8), that is, with the cutting tube 2 not inserted in the central canal 12 or removed from it, are contiguous with one another and securely insulate the central canal 12.

To prevent the blade 2a of the cutting tube 2 from striking its sharp front cutting edge against the flap wings 14a and damaging them when the cutting tube 2 is pushed through the central 2 o the flap valve 14, as shown in FIG. 9, the angle at which the two flap wings 14a of the flap valve 14 are contiguous with one another is selected to be smaller than the angle of the blade 2a on the distal end of the cutting tube 2. The selection of this angle of the mutually contiguous flap wings 14a, which is beak-shaped, ensures that when the cutting tube 2 is introduced into the flap valve 14, the proximal ends of the blade tapering of the blade 2a of the cutting tube 2 open outward primarily in radial direction. The beak-shaped configuration of the flap wings 14a here signifies that the distal ends of the flap wings 14a, contiguous to one another, are bent from the instrument's axis 4 externally outward and are contiguous to one another in the area of these bendings.

In the open position of the flap valve 14, shown in FIG. 9, the cutting tube 2 inserted in the central canal 12 insulates the central canal 12 because, at least in the area of the flap valve 14, the outer diameter of the cutting tube 2 essentially corresponds to the inner diameter of the central canal 12.

An additional possibility for providing gas-proof insulation of the central canal 12 in the area of the cutting tube 2 is to configure a thickened area 11a on the inserted instrument 11 in the area of the distal end of the additional medical instrument 11 inserted into the cutting tube 2, which thickened area corresponds to the inner diameter of the cutting tube 2, especially in the area of the blade 2a, as can be seen from FIG. 6.

Besides the insulating effect of the thickened area 11 a, this thickened area 11a of the additional medical instrument 11 can be used as a cutting edge guard, which on introducing the cutting tube 2 into the operating area, can be brought into contact flush with the cutting edge of the blade 2a and locks in the axial direction, at least flush with the cutting edge, or overhangs the cutting edge 2a on the distal side in order to prevent damage to tissue that is to be protected.

Figure 10:
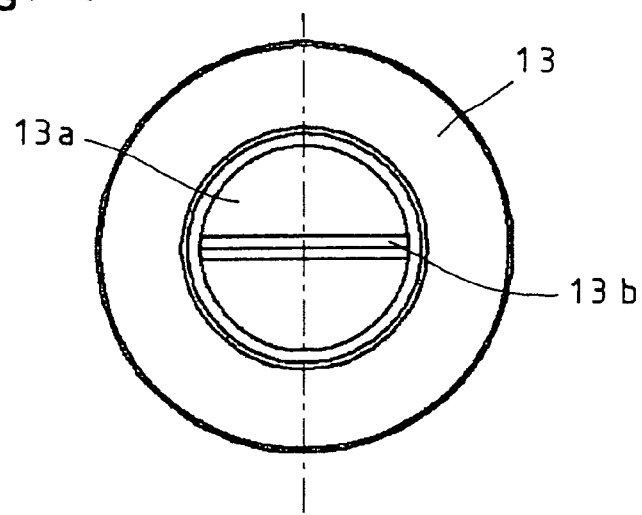
FIG. 10 shows a schematic aerial view of an inventive insulation cap.

The insulation cap 13 for closing the proximal end of the central canal 12 is advantageously configured as a one-time valve consisting of an autoclavable material, whose insulation agent 13a, when the additional medical instrument 11 is pushed into the central canal 12, is contiguous with the shaft of the inserted instrument 11 and serves as insulation. In the embodiment of the insulation cap 13 illustrated in FIG. 10, a slit 13b is made in the insulation agent 13a which is widened by the insertion of the instrument 11.

According to an alternative embodiment of the insulation cap 13, which is not illustrated, the insulation agent 13a is configured as a membrane that can be perforated by the instrument 11 that can be inserted into the central canal 12.

Figure 4:
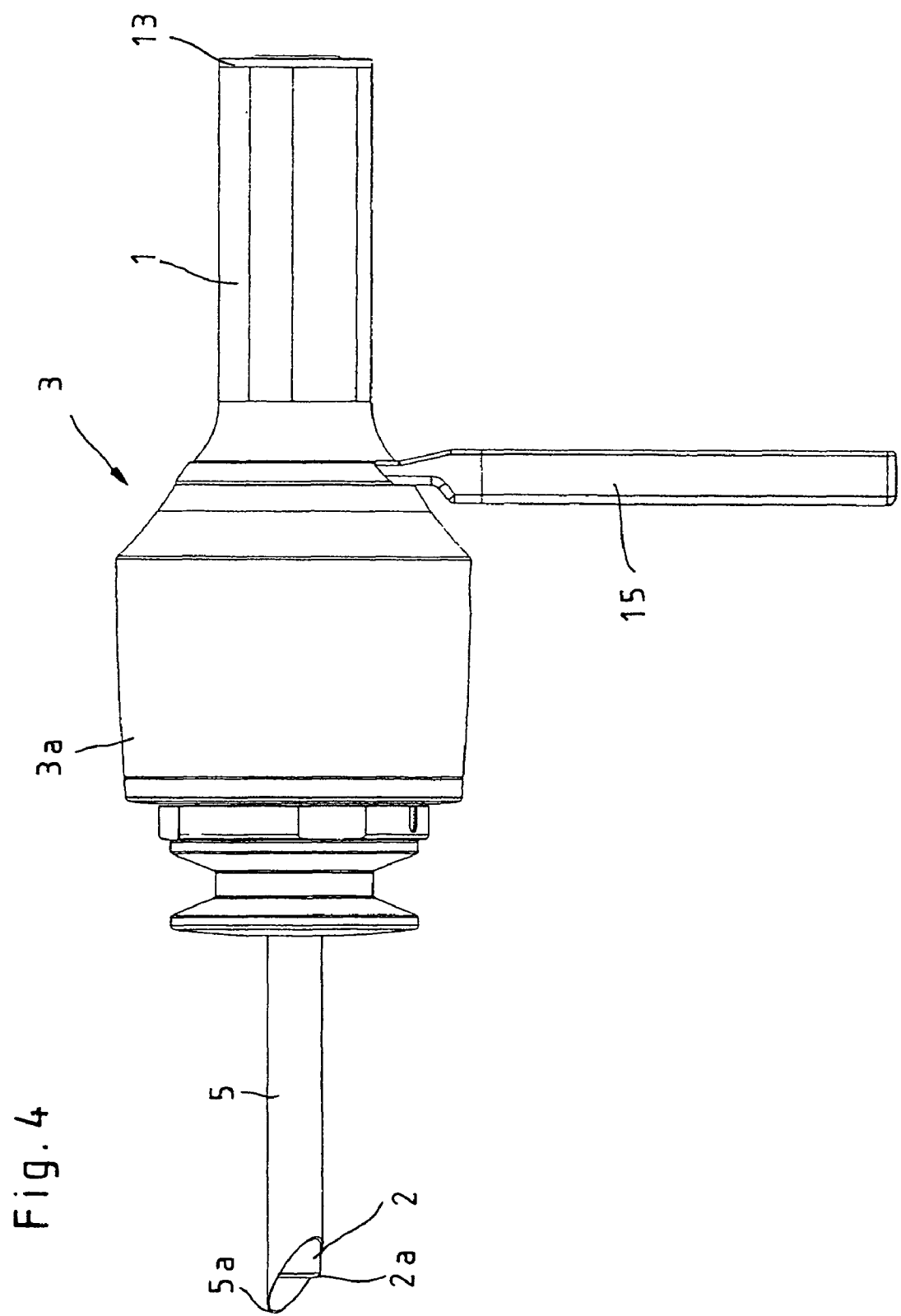
FIG. 4 shows a side view of the instrument according to FIG. 3 in assembled condition.

As can further be seen from FIGS. 3, 4, and 6, an additional, angled hand grip 15 is secured on the handle 1 to facilitate control of the morcellator for the operator. This additional handgrip 15, as illustrated, is preferably at a 90-degree angle to the instrument's longitudinal axis. Of course, depending on the area of application and/or the operator's wishes, and/or ergonomic considerations, the additional handgrip can also be positioned at other angles. Particularly if the additional handgrip 15 is of metal construction, weight-optimized configuration of the handgrip 15 is important for reducing the instrument's total weight. For this purpose it is possible, for instance, to configure the handgrip 15 in such a way that in its center area 15a it has a complete open passage or else, s seen in FIG. 3, a return.

Figure 7:
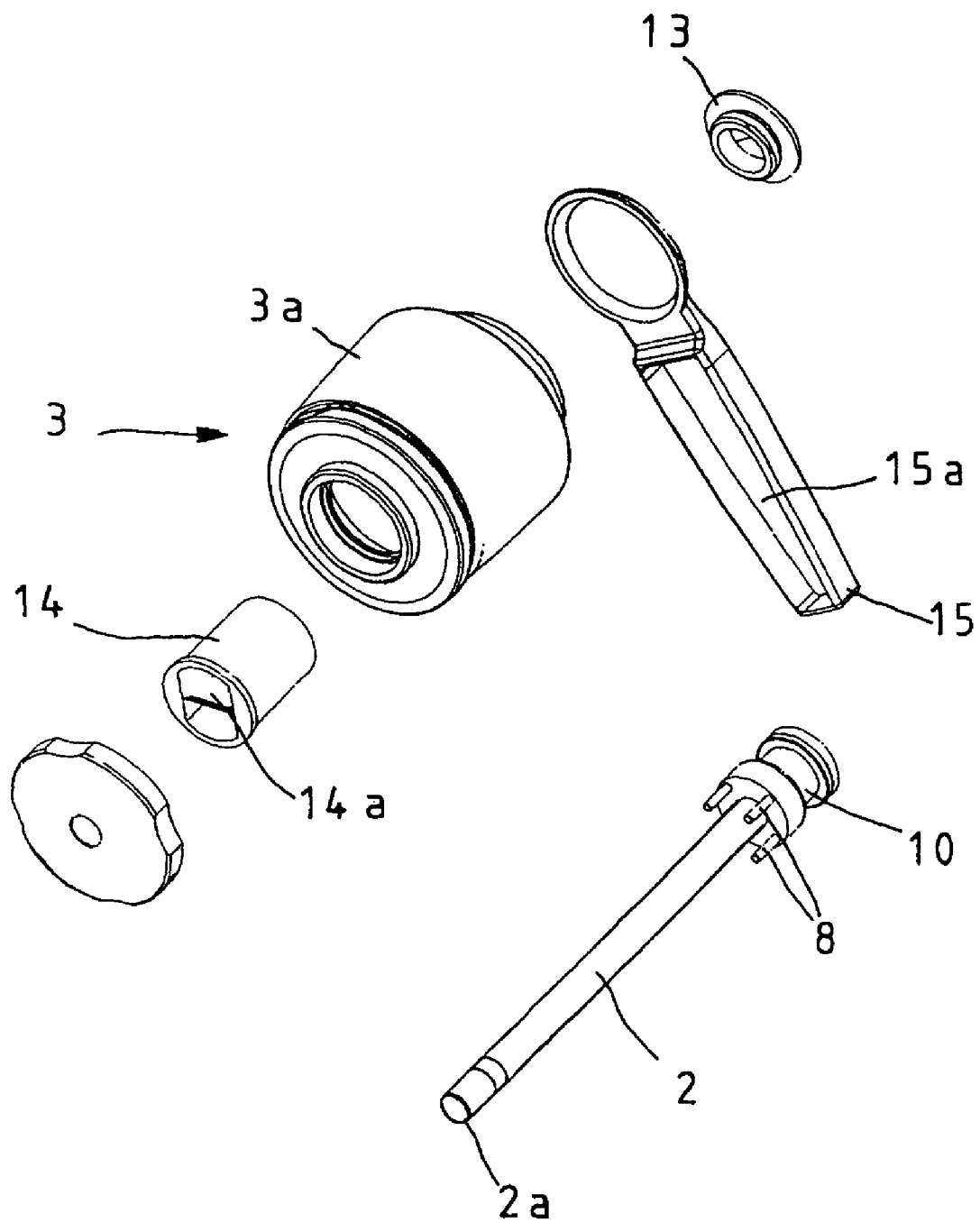
FIG. 7 shows a perspective exploded view of a second practical embodiment of an inventive instrument.

FIG. 7 depicts a second practical embodiment for configuring a medical instrument for cutting biological and especially human tissue that takes the form of a morcellator. This morcellator serving for supra-cervical interventions is distinguished from the morcellator for laparoscopic interventions, as described in particular with reference to FIGS. 3, 4, and 6, in that the latter has no trocar sleeve 5 surrounding the cutting tube 2 on the distal side and has no distinct handle 1. Instead, as already described with reference to FIG. 1, the engine housing 3a serves as a handle 1.

What is claimed is:

1. A medical instrument for cutting biological tissue, having a hollow cutting tube that can rotate about its longitudinal axis by means of an engine, on whose distal end at least one blade is mounted, and also having a handle in which the cutting tube is mounted for guiding the instrument, and with the engine configured as a hollow-shaft engine positioned on the cutting tube, distinguished in that the cutting tube is powered to rotate about the longitudinal axis thereof because the hollow cutting tube and the hollow-shaft engine are coupled with one another by means of a coupling mechanism positioned on the hollow cutting tube for transmitting the rotation of the hollow-shaft engine onto the hollow cutting tube, with the coupling mechanism having rods running in the axial direction of the cutting tube, which rods are positioned on the cutting tube and/or positioned on the hollow-shaft engine, and which are insertable into corresponding openings in the other respective component.

2. A medical instrument according to claim 1, distinguished in that four rods are positioned at equal distances around the longitudinal axis of the cutting tube and running in the axial direction of the cutting tube, and on the hollow-shaft engine at least four openings are formed for inserting the rods.

3. A medical instrument according to claim 1, distinguished in that the rods that couple the cutting tube and the hollow-shaft engine to one another are positioned on an adapter that can be secured on the cutting tube.

4. A medical instrument according to claim 1, distinguished in that the cutting tube can be powered directly and gearlessly by means of the hollow-shaft engine.

5. A medical instrument according to claim 1, distinguished in that the hollow-shaft engine is configured as an outer rotor engine.

6. A medical instrument according to claim 5, distinguished in that a rotor of the outer rotor engine coaxially surrounds the cutting tube and the cutting tube forms a stator of the outer rotor engine.

7. A medical instrument according to claim 6, distinguished in that the cutting tube consists of a magnetizable material and the winding of the outer rotor engine coaxially surrounds the cutting tube.

8. A medical instrument according to claim 1, distinguished in that the cutting tube is mounted in the engine housing by means of at least one bearing.

9. A medical instrument according to claim 8, distinguished in that at least one bearing is configured as an angular contact ball bearing or a taper roller bearing that accepts axial forces.

10. A medical instrument according to claim 1, distinguished in that the cutting tube is positioned on the distal side in a trocar sleeve coaxially surrounding the cutting tube.

11. A medical instrument according to claim 1, distinguished in that the handle has a central passage bore hole, which on the proximal side forms an extension of the hollow cutting tube.

12. A medical instrument according to claim 1, distinguished in that an additional, angled handgrip is securable on the handle.

13. A medical instrument for cutting biological tissue, comprising a hollow outer shaft tube having a central canal extending along a longitudinal axis thereof for inserting a hollow cutting tube that rotates about its longitudinal axis by means of an engine and on whose distal end at least one blade is positioned, as well as for inserting at least one additional medical instrument that is insertable into the hollow cutting tube, wherein at least one insulation means is provided for gas-proof insulation of the central canal of the hollow outer shaft tube, distinguished in that the at least one insulation means is configured as a flap valve having two flap wings and that is insertable into the central canal of the hollow outer shaft tube and whose two flap wings pointing toward the distal end of the central canal are contiguous to one another at an angle that is smaller than the angle of the blade on the distal end of the cutting tube that is insertable into the central canal and in that in the position with the cutting tube being inserted in the central canal the two flap wings of the flap valve are positioned on the outer surface of the cutting tube.

14. A medical instrument according to claim 13, distinguished in that an insulation cap is securable on the proximal end of the central canal as an additional insulation agent.

15. A medical instrument according to claim 14, distinguished in that the insulation cap is configured as a membrane that can be perforated by the medical instrument that is insertable into the central canal.

16. A medical instrument according to claim 14, distinguished in that in the insulation cap an opening is made which can be widened by the medical instrument that is insertable into the central canal.

17. A medical instrument according to claim 14, distinguished in that the insulation cap is configured as a one-time valve that comprises autoclavable material.

18. A medical instrument according to claim 13, distinguished in that the outer diameter of the cutting tube corresponds essentially to the inner diameter of the central canal.

19. A medical instrument according to claim 13, distinguished in that, to configure the central canal, the instrument includes at least one trocar sleeve mounted on the distal side, an engine configured as a hollow-shaft engine and equipped with a central opening for the cutting tube that is to be powered, as well as a handle positioned on the proximal side and equipped with a central passage bore hole.

* * * * *